United States Patent [19]

Brown et al.

[11] Patent Number: 5,016,648

[45] Date of Patent: May 21, 1991

[54] LIMB PROTECTIVE COVERING

[76] Inventors: Ronald E. Brown, 2207 Bowman La., Franklin, Tenn. 37064; Jack M. Grinwis, 7354 La Costa Dr., Hudson, Ohio 44236

[21] Appl. No.: 485,140

[22] Filed: Feb. 23, 1990

[51] Int. Cl.$^5$ .............................................. A61F 13/00
[52] U.S. Cl. .................................. 128/846; 128/878; 128/879
[58] Field of Search ................ 128/82, 83, 157, 856, 128/D15, 846, 878, 879; 2/16, 59, 60, 61, 62, 22

[56] References Cited

U.S. PATENT DOCUMENTS

| | | | |
|---|---|---|---|
| 2,229,575 | 1/1941 | Kaplan | 128/83 |
| 3,824,998 | 7/1974 | Snyder | 128/856 |
| 4,036,220 | 7/1977 | Bellasalma | 128/856 |
| 4,224,935 | 9/1980 | Metelnick | 128/82 |
| 4,254,765 | 3/1981 | Brown et al. | 128/82 |
| 4,330,887 | 5/1982 | White | 2/16 |
| 4,346,699 | 8/1982 | Little et al. | 128/82 |
| 4,363,317 | 12/1982 | Broucek | 128/82 |
| 4,523,586 | 6/1985 | Couri | 128/82 |
| 4,530,350 | 7/1985 | Brown et al. | 128/82 |

*Primary Examiner*—Robert A. Hafer
*Assistant Examiner*—Charles H. Sam
*Attorney, Agent, or Firm*—Mark J. Patterson; Edward D. Lanquist, Jr.

[57] ABSTRACT

A limb protective covering having a tubular sleeve of waterproof material for receiving a limb and elongated closure member for tightening the sleeve around the limb. A portion of the sleeve above the closure member is folded over the closure member to form a cuff. A belt attaches to the cuff and wraps around the cuff to completely seal the covered limb.

10 Claims, 2 Drawing Sheets

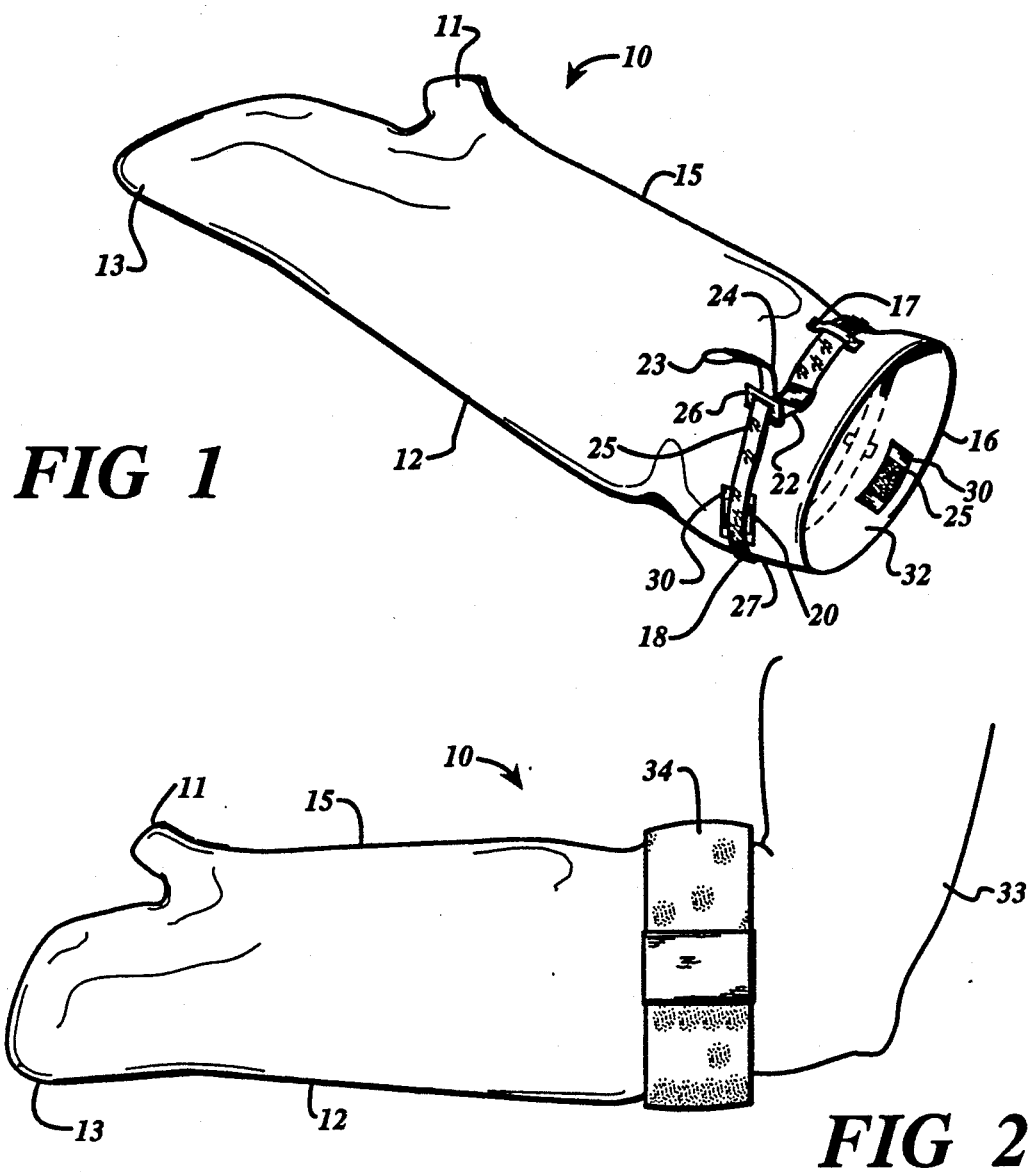
FIG 1
FIG 2
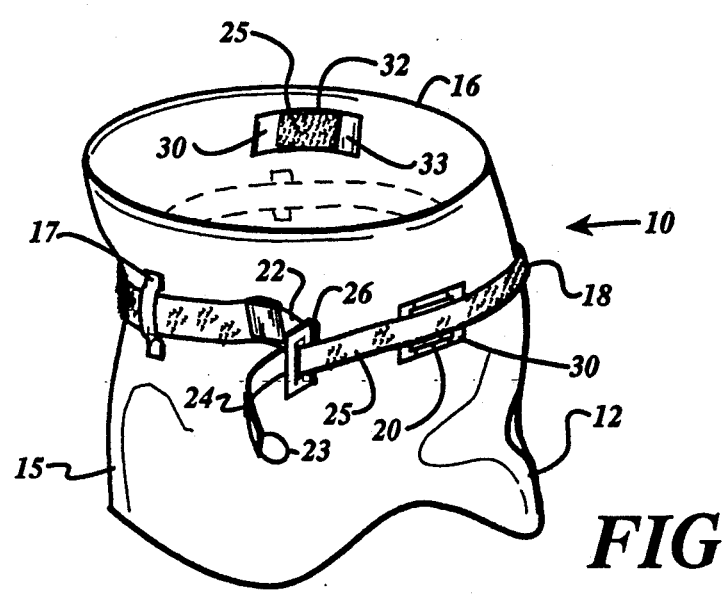
FIG 3

LIMB PROTECTIVE COVERING

BACKGROUND OF THE INVENTION

The present invention relates generally to a limb protective covering and particularly to a waterproof protective covering for bandaged or injured portions of arms and legs.

It will be appreciated by those skilled in the art that an injured limb that is bandaged or in a cast must be kept dry to avoid disintegration of the cast or infection of the wound. Furthermore, water on some wounds will cause extreme pain to the injured person. However, injured persons must still bathe, shower, and be exposed to rain. To this end, there have been several attempts to provide a limb protective covering.

The first attempts to provide waterproof limb protectors are illustrated in the following art: U.S. Pat. No. 4,244,935 issued to Mettelnick; U.S. Pat. No. 4,363,317 issued to Broucek; U.S. Pat. No. 4,562,834 issued to Bates et al.; U.S. Pat. No. 4,727,864 issued to Wiesenthal et al.; U.S. Pat. No. 4,036,220 issued to Bellasalma; U.S. Pat. No. 3,747,125 issued to Goldman et al.; U.S. Pat. No. 4,043,326 issued to Little et al.; U.S. Pat. No. 3,906,941 issued to Cook; U.S. Pat. No. 2,244,871 issued to Guinzburg; U.S. Pat. No. 1,980,480 issued to King; U.S. Pat. No. 3,741,203 issued to Liman; U.S. Pat. No. 3,735,759 issued to MacKay; and U.S. Pat. No. 3,785,374 issued to Lipsom. Unfortunately, these prior illustrations are either too expensive and complex or are inadequate to maintain a waterproof seal. Liman, Bellasalma, Mettelnick, Broucek, and Bates et al. each disclose the use of a strap encircling the cast shield at the top proximate to the opening. However, the use of a single strap has been found to be inadequate to keep the cast or bandage entirely dry and can often lead to "guttering" when a fold in the cover actually holds water that flows onto the cast or bandage during removal.

U.S. Pat. Nos. 4,254,765 and 4,530,350 issued to Brown and Grinwis attempted to achieve a better seal by providing an adjustable strap away from the opening. U.S. Pat. No. 4,098,268 issued to Scott also places the strap away from the opening. Although these patents have improved the seal at the opening, the problem of "guttering" was neither recognized nor corrected.

Also, none of these previously cited examples fully solve the problems associated with one-hand placement. If the hand or arm of the user is bandaged or in a cast, the user of the limb protective covering will have only one arm available for tightening the opening around the limb. If elastic is used to tighten the opening around the arm, one-arm placement can cause much pain, because the elastic will rub against the cast or bandage while the limb is placed in the opening. Also, the devices of the prior art are either difficult to put on with one arm or cannot be effectively tightened with one arm.

Further, a single strap on a protective limb covering will still allow the strap to "ride" toward and into the bandage or cast. This riding is caused by movement of the limb.

What is needed, then, is a limb protective covering that is very inexpensive to produce, yet free of the "guttering" problems not recognized in the prior art. Also, a limb protective covering is needed that can be used comfortably and conveniently with only one hand. Further, a limb protective covering is needed that does not "ride" up and down the limb. This needed limb protective covering must provide an excellent seal regardless of the size or shape of the covered limb. This consistent protection is lacking in the prior art.

SUMMARY OF THE INVENTION

In the present invention of a limb protective covering, an elongated and generally tubular, flexible, waterproof member is provided having at one end a foot or hand receiving member and at the other end an opening for receiving the limb to be covered. A closure member is attached to the outer wall of the sleeve of the elongated waterproof member a small distance below the opening. The closure member encircles the covered limb and attaches to the outer wall at an outside panel member. The closure member has a first strap member and a second strap member extending from opposite ends of the outer panel member. The first strap member has a rigid hook on the end remote from the panel so that the hook receives the remote end of the second strap member. The second strap member has hook and loop fabric on it so that after placement through the hook, the second strap member can be tightened around the covered limb for attachment to itself. An outer rigidifying panel can be used in conjunction with the outer panel member to support the wall portion of the elongated waterproof member. Loops are provided on the outer wall of the elongated sleeve to accept and direct the closure member.

After the closure member is tightened around the covered limb, the elongated waterproof member above the closure member is folded down over the closure member, thereby forming a cuff and exposing an inner panel member attached to the inner wall of the sleeve. In the preferred embodiment, the inner panel member is covered with hook and loop fabric. A belt is provided with hook and loop fabric on each end and has a rubber first side and a hook and loop fabric second side. The first end of the belt is releasably attached to the inner panel member with first side facing inwardly by use of the hook and loop fabric. The belt is then wrapped tightly around and above the fold of the cuff to create a completely waterproof seal that is not subject to "riding". The second end is then attached to the second side of the taut belt.

Accordingly, an object of the present invention is to provide a limb protective covering that is convenient for one-handed application.

Still another object of the present invention is to prevent the guttering associated with a single-strap protective limb covering.

A further object of the present invention is to provide a limb protective covering that is essentially water tight.

A still further object of the present invention is to provide a limb protective covering that does not ride up and down the limb to be covered.

BRIEF DESCRIPTION OF THE DRAWINGS

FIG. 1 is a perspective view of a hand and arm protective covering prior to the cuff being folded over the closure member.

FIG. 2 is a side elevation view of the lower arm and hand enclosed in the protective cover of the present invention.

FIG. 3 is an enlarged view of the top of the protective covering of FIG. 1 showing the closure member in operation.

DESCRIPTION OF THE PREFERRED EMBODIMENT

Figure 4:
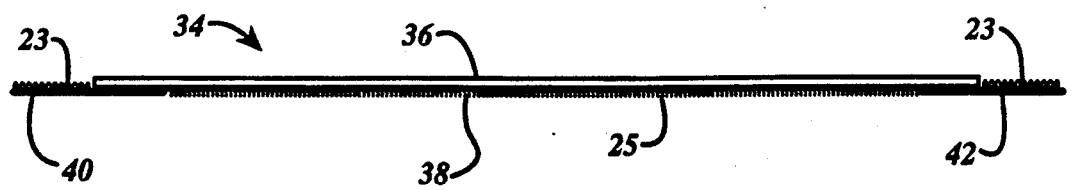
FIG. 4 is a side view of the belt of the present invention.

Referring now initially to FIG. 1, there is shown generally at 10 the arm and hand embodiment of the limb protective covering of the present invention. In the preferred arm and hand embodiment, limb protective covering 10 has elongated and generally tubular, flexible, waterproof member 15. In the preferred embodiment, elongated member 15 has thumb portion 11, finger portion 13, and elongated tubular sleeve 12 and is made of polyurethane plastic. However, elongated tubular member 15 can be constructed from any waterproof and flexible material. Also, distinct finger portion 13 and thumb portion 11 are not required in practice. Closure member 18 is attached to the outer wall of sleeve 12 below opening 16 at outer panel 20. In the preferred embodiment, closure member 18 is fixed to sleeve 12 by heat sealing. However, any method of water resistant attachment can be used. Closure member 18 has first member 22 and second member 24. In the preferred embodiment, closure member 18 is received and directed by loops 12. Also, in the preferred embodiment, first member 22 is provided with rigid hook 26 which receives second member 24. Second member 24 passes through hook 26 and attaches back upon itself with male hook and loop fabric 23 and female hook and loop fabric 25 after closure member 18 is tightened around arm 33. In the preferred embodiment, hook and loop fabric 23 25 is used. However, in practice, any type of releasable connection between first member 22 and second member 24 can be used that allows closure member 18 to be tightened around the limb.

After closure member 18 is tightened, the portion of sleeve 12 above closure member 18 is folded down to cover closure member 18, thereby creating cuff 27 and exposing inner panel 32 as shown in FIGS. 1-3. Inner panel 32 is heat sealed to cuff 27 in the preferred embodiment. Rigidifying member 33 can be added to inner panel 32 to strengthen inner panel 32. Rigidifying member 30 can be added to outer panel 20 to strengthen outer panel 20.

Referring now to FIG. 4, there is shown generally at 34 the belt of the preferred embodiment. Belt 34 has first side 36, second side 38, first end 40, and second end 42. First and second ends 40 and 42 are attached by heat sealing to second side 38 of belt 34. As can be seen by reviewing FIGS. 1-4, first end 40 releasably attaches to inner panel member 32. Belt 34 is then wrapped around arm 33 with first side 36 facing inwardly. After belt 34 is tightened, second end 42 attaches to second side 38 of belt 34. In the preferred embodiment, first end 40 and second end 42 are covered with male hook and loop fabric 23 while second side 38 and inner panel 32 are covered with female hook and loop fabric 25. First side 36 is an elastomeric material which is, in the preferred embodiment, neoprene rubber. In the preferred embodiment, belt 34 is wider than cuff 27.

Figure 5:
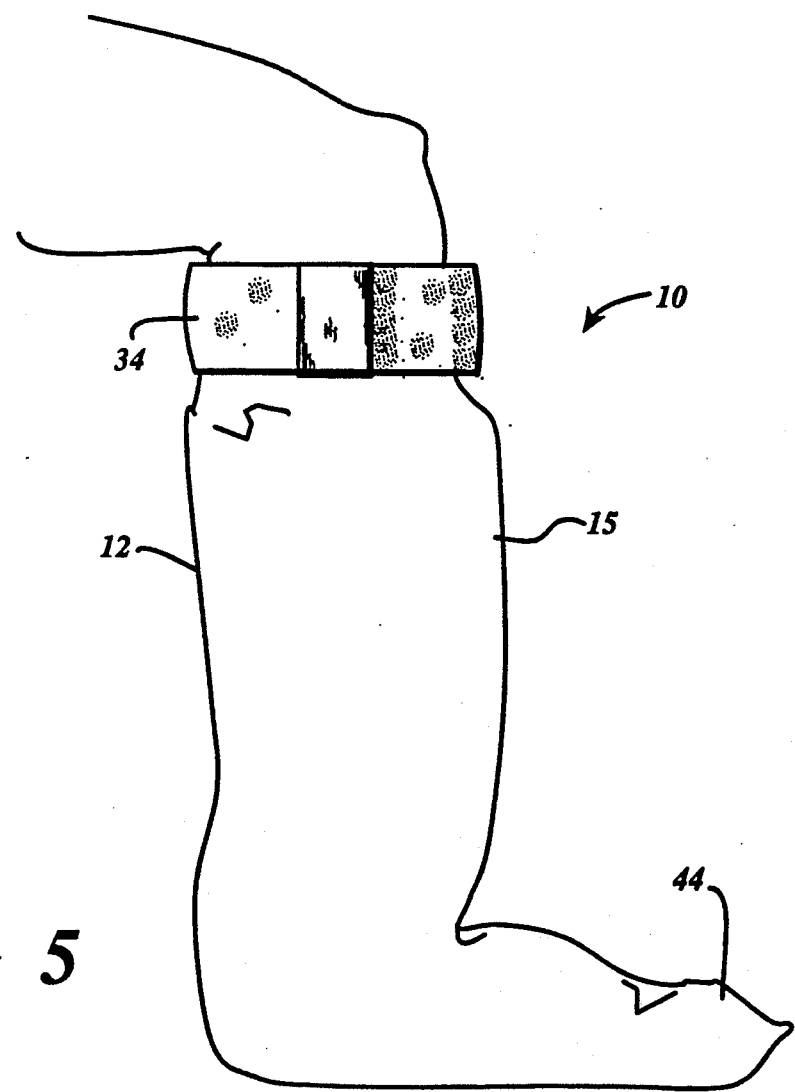
FIG. 5 is a side view of the lower leg and foot enclosed in the protective limb covering of this invention.

FIG. 5 shows generally at 10 the leg and foot embodiment of the limb protective covering of the present invention. The essential difference between FIG. 1 and FIG. 5 is that FIG. 5 has foot portion 44, whereas FIG. 1 has thumb portion 11 and finger portion 13.

Using the limb protective covering 10 over arm 33 as an example, arm 33 is inserted through opening 16 until hand (not shown) fills thumb portion 11 and finger portion 13. Closure member 18 is tightened around arm 33. Second member 24 passes through rigid hook 26 at end of first member 22 and fastens against itself. The portion of sleeve 12 above closure member 18 is cuff 27 folded over closure member 18 exposing inner panel 32. First end 40 of belt 34 releasably attaches to panel 32. Belt 34 is then wrapped around arm 33. When tight, second end 42 is releasably attached to second side 38.

What I claim is:

1. A protective covering for a limb comprising:
   a. an elongated, generally tubular, flexible, and waterproof member closed at one end and having an opening at another end for receiving said limb, said elongated tubular member also having a sleeve, said sleeve comprising an inner wall and an outer wall;
   b. an elongated closure member attached to said sleeve below said opening on said outer wall, said closure member having a first end and a second end;
   c. said closure member first end and second end releasably attached together for tightening said sleeve around said limb;
   d. a cuff exposed and defined by folding said sleeve above said closure member over said closure member;
   e. an inner panel attached to said inner wall of said sleeve; and
   f. a belt encircling said limb releasably attached to said inner panel.

2. The protective limb covering of claim 1 wherein said belt comprises:
   a. a first side;
   b. a second side;
   c. a first belt end fixedly attached to said second side and adapted to releasably connect to said inner panel;
   d. a second belt and fixedly attached to said second side and adapted to releasably attach to said second side.

3. The protective limb covering of claim 2 wherein:
   a. said closure member is heat sealed to said outer wall of said sleeve; and
   b. said inner panel member is heat sealed to said inner wall of said sleeve.

4. The protective limb covering of claim 2 wherein said second end of said closure member attaches to said first end of said first closure member by hook and loop fabric.

5. The protective limb covering of claim 2 wherein said second end attaches to said first end by hook and loop fabric.

6. The protective limb covering of claim 2 wherein the tubular member is polyurethane.

7. The protective limb covering of claim 2 wherein said tubular member comprises a foot receiving member integral therewith.

8. The protective limb covering of claim 2 wherein said tubular member comprises a hand receiving member integral therewith.

9. The protective limb covering of claim 2 wherein:
   a. said first side is heat sealed to said second side; and
   b. said first belt end and said second belt end are heat sealed to said second side.

10. The limb protective covering of claim 2 further comprising a rigidifying panel at the point of attachment between said belt and said sleeve.

* * * * *